United States Patent [19]

Wilkinson

[11] 4,114,603

[45] Sep. 19, 1978

[54] INTRACRANIAL PRESSURE MONITORING CATHETER

[76] Inventor: Harold A. Wilkinson, 330 Brookline Ave., Boston, Mass. 02215

[21] Appl. No.: 712,132

[22] Filed: Aug. 6, 1976

[51] Int. Cl.$^2$ ............................................. A61B 5/00
[52] U.S. Cl. ............................. 128/2 R; 128/2.05 E; 128/348
[58] Field of Search .......... 128/2 R, 2 N, 2 S, 2.05 E, 128/2.05 N, 2.05 P, 2.05 S, 350 R, 350 V, 2.05 D, 348; 73/388 R

[56] References Cited

U.S. PATENT DOCUMENTS

| 3,669,094 | 6/1972 | Heyer ................................. 128/2 R |
| 3,789,667 | 2/1974 | Porter et al. ................ 128/2.05 D X |
| 3,877,137 | 4/1975 | Hakim et al. ........................... 29/463 |
| 3,886,948 | 6/1975 | Hakim ............................... 128/350 V |

OTHER PUBLICATIONS

Numoto et al., "Pressure Indicating Bag for Monitoring Intracranial Pressure", J. Neurosurg., vol. 39, p. 784–787.

Journal of Neurosurgery, vol. 39 (Sep. 1973), p. 416, by John K. Vries.

Primary Examiner—Robert W. Michell
Assistant Examiner—Michael H. Thaler
Attorney, Agent, or Firm—Kenway & Jenney

[57] ABSTRACT

The cerebro-spinal-fluid pressure monitoring device disclosed herein employs a flexible, ribbon-like distal portion providing generally parallel front and back surfaces. The front surface has a recess near the distal tip of the catheter so that when the tip of the catheter is inserted between the dura mater and arachnoid membrane, with the back face of the catheter supported by the patient's skull, the arachnoid membrane bridges the recess. A longitudinal lumen communicates between the recess and a pressure monitoring device for providing a pressure transmitting fluid coupled therebetween. The ribbon-like distal portion is of essentially constant cross-sectional shape and is of sufficient length to permit the catheter to exit the scalp through an incision spaced from the point at which the catheter passes through the skull. This design enables the catheter to be removed by being drawn longitudinally from the point of exit from the scalp.

7 Claims, 2 Drawing Figures

INTRACRANIAL PRESSURE MONITORING CATHETER

BACKGROUND OF THE INVENTION

This invention relates to catheters useful for continuously monitoring the pressure of cerebro spinal fluid in a patient.

Various devices are currently available for monitoring intracranial cerebro spinal fluid (CSF) pressure in patients exhibiting symptoms of brain damage. The monitoring of CSF pressure is indicated where the surgeon suspects the presence of cerebral edema, an obstruction of normal CSF flow, blood clots, tumors, or other causes of increased pressure in the head of a patient. In many of these situations, it has been found that measurement of intracranial CSF pressure, as well as fluctuations in the pressure, can be exceedingly useful as a diagnostic tool, and that such measurements can yield valuable information when made either prior to or after craniotomy.

One type of pressure monitoring devices currently available comprises a fluid-filled, pressure indicating bladder which is placed within the skull, and is connected via a fluid couple to a pressure monitoring device. Examples of this type of device are disclosed in the Journal of Neurosurgery, Vol. 39 (Dec. 1973) at page 784, and in U.S. Pat. No. 3,877,137 to Hakim et al. Minaturized electronic transducers which may be implanted in the brain and electrically connected to the outside, as well as telemetric devices which require no direct connection to the exterior of the skull have also been proposed. These latter types of devices, having no fluid couple, are characterized by a potentially reduced infection risk, but also by the liklihood of electronic drift which results in instability and unreliability of the measurements they produce. Further, use of the telemetric type of device typically requires the head to be opened twice, once for insertion and once for withdrawal.

A serious problem in all of these devices is the possibility of infection. Whenever an incision is made through the scalp of a patient, there is a possibility that a staph or other infection may occur at the locus of the incision. Accordingly, when a short, direct tunnel through the scalp and skull is maintained over the period of monitoring, a path may be provided for the infection to migrate to the subdural space. Even more seriously, if the arachnoid membrane encasing the brain is penetrated, there is a possibility of infection within the brain itself.

Another type of monitoring device is described in the Journal of Neurosurgery, Vol. 39 (Sept. 1973) at page 416, wherein John K. Vries et al disclose a subarachnoid screw for monitoring intracranial pressures. This device comprises a hollow tubular metal structure designed to communicate between the subarachnoid space and the outside of the scalp. The proximal end of the screw consists of a standard luer lock and a hexogonal collar. The distal end has an open tip. Threads are provided adjacent the distal opening. To install the device, an incision is made in the scalp and a ¼ inch hole is drilled through the skull. Prior to inserting the screw, the exposed dura is nicked with a knife and removed with a small angled curette. This maneuver usually also opens the arachnoid membrane, and a small amount of CSF is usually seen. The screw is then threaded into the hole so that its distal opening is in direct communication with the patient's CSF. In some cases, the arachnoid membrane is allowed to bridge the end of the hollow screw.

In use, the proximal end of the screw is connected to a stopcock assembly via a saline-filled extension tube. The stopcock connections include a pressure transducer, a 20 cc syringe filled with saline, and a water manometer which is open to the air through a bacteriologic filter. The output of the transducer is displayed on an oscilloscope and recorded on chart paper. The system is calibrated by zero balancing the transducer to the water manometer after matching up the height of the water manometer to the level of the end of the screw in the subarachnoid space. The transducer is then opened to the subarachnoid space via the saline-filled extension tube, and a calibrated intracranial pressure is recorded.

While the simplicity of this device makes it attractive, its use nevertheless still involves a significant infection risk since direct communication is established between the patient's subdural or subarachnoid space and the exterior of the scalp. On removal of the screw, the skin wound is sutured, but any infection which may occur at the wound during the monitoring procedures or thereafter has a short path to the interior of the skull.

SUMMARY OF THE INVENTION

The instant invention provides an intracranial pressure monitoring catheter which employs the arachnoid membrane as a sensing membrane for monitoring CSF pressure. The catheter comprises a flexible, generally flat, ribbon-like, elongate distal portion having front and back surfaces and an essentially constant cross-sectional shape. A recess is provided near the distal tip of the front surface of the flat portion, and the catheter has a longitudinal lumen for providing a fluid couple between the recess and a pressure monitoring device.

To install the catheter, a first incision is made in the scalp and an aperture is formed which penetrates the skull and dura mater, but not the arachnoid membrane. A second scalp incision, spaced apart from the first, is then opened and a subcutaneous tunnel is formed between the incisions. The catheter is then introduced through the second incision, passed through the subcutaneous tunnel and the aperture in the skull, and is inserted into the subdural space, i.e., between the arachnoid membrane and dura mater, with the opening of the recess being bridged by the arachnoid membrane. The back of the catheter is supported by the patient's skull. The incision above the skull hole is then closed, and the proximal end of the catheter is attached to a suitable pressure measuring device.

When the catheter lumen and recess are filled with fluid, a fluid couple is provided between the portion of the arachnoid membrane bridging the sensing recess and the pressure measuring device. Fluctuations in CSF pressure, even those caused by heart beats and normal respiration, are readily detectable. On conclusion of the pressure monitoring, the catheter is withdrawn by pulling on a portion of the catheter external to the scalp. Since the cross-section of the distal portion is essentially constant, it may be withdrawn relatively easily.

A primary object of the invention is to provide a pressure monitoring catheter which significantly reduces the possibility of infection. This object is realized because the catheter of the invention does not require that the arachnoid membrane be penetrated and because the scalp entrance incision and skull entrance hole are spaced apart along the skull. Thus, use of catheter does not require that a short passage be maintained through both the scalp and the skull at one location.

Another object of the invention is to provide a simple and inexpensive catheter which can measure static pressure, is sensitive to small pressures changes, and employs the arachnoid membrane as a pressure responsive membrane.

Other objects and features of the invention will be apparent to those skilled in the art from the following description of a preferred embodiment and from the drawing.

BRIEF DESCRIPTION OF THE DRAWING

Corresponding reference characters indicate corresponding parts in the several views.

DESCRIPTION OF THE PREFERRED EMBODIMENT

Figure 1:
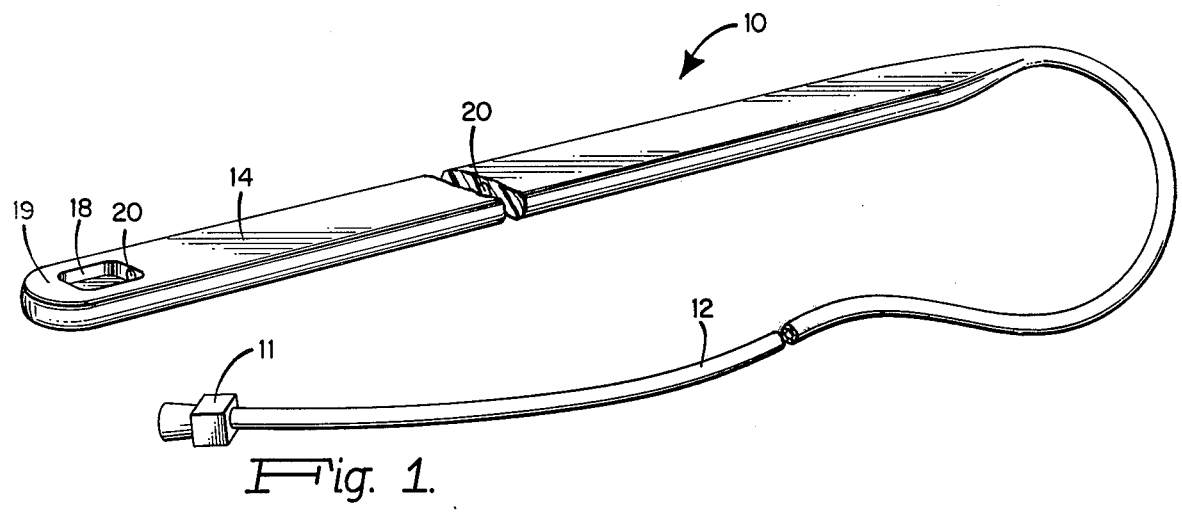
FIG. 1 is a partially broken away perspective view of the catheter of the invention.
Figure 2:
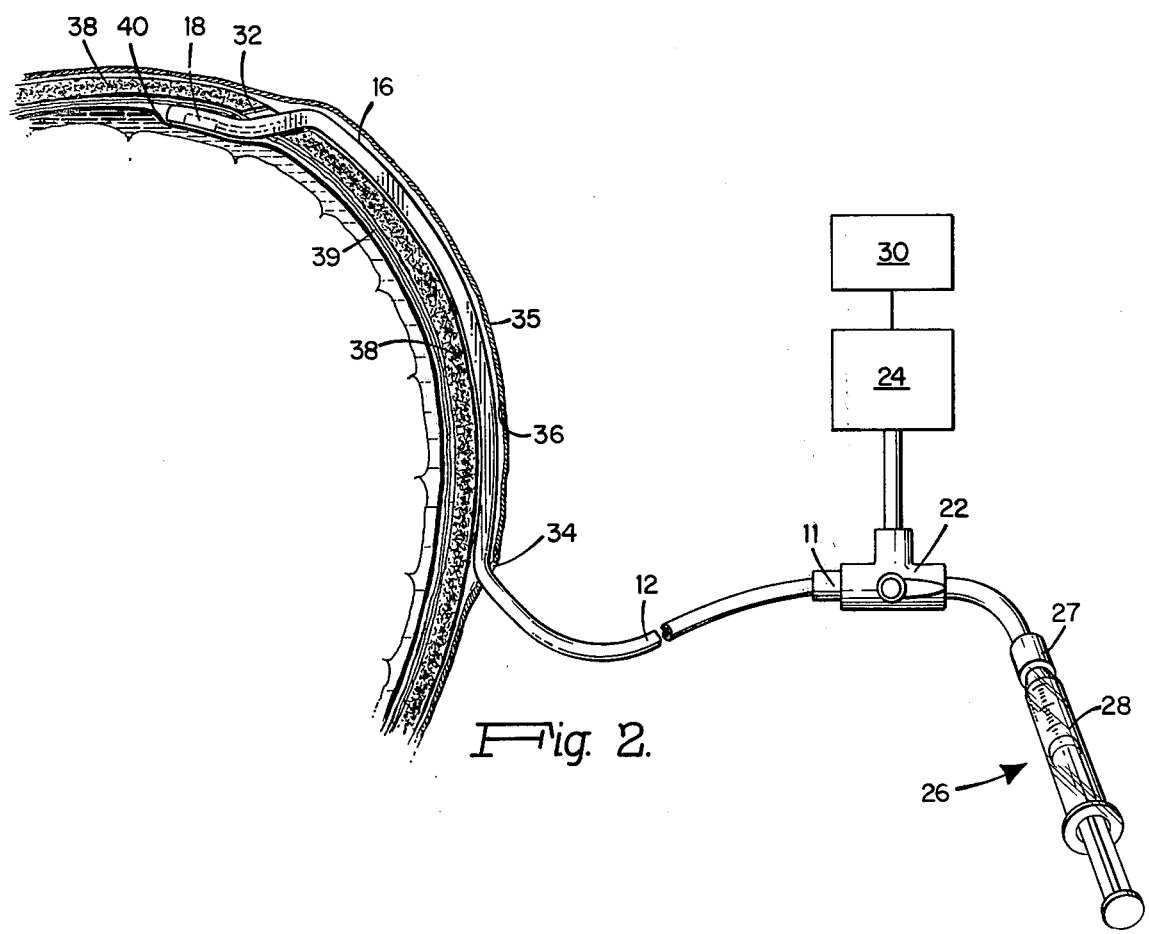
FIG. 2 is a cross section of the catheter of the invention as installed in the cranium of a patient.

Referring to the drawing, a catheter is shown which comprises a generally flat or ribbon-like distal portion 10 connected to a length of tubing 12 which terminates, at the proximal end of the catheter, with a connection luer hub 11. The distal portion 10 is preferably fabricated from a flexible, easily sterilizable material, e.g., medical grade silicone rubber such as that commercially available under the trademark "Silastic". Preferably, at least parts of the catheter are made radio-opaque to permit its location to be determined by x-ray. The distal portion 10 has front and back surfaces 14, 16 and includes a cup-like recess 18, positioned in the front surface 14 adjacent the catheter's distal tip. The flat front surface 14 defines a sealing surface 19 about recess 18. A lumen 20 passes through the distal portion 10 and communicates between the recess 18 and the interior of the tubing 12.

A three-way stopcock 22 is attached to a luer hub 11 and may be adjusted to communicate with a pressure measuring device 24, i.e., a standard physiological transducer, or a fluid injection means 26, which may comprise a luer hub 27 fitted with a syringe 28. The pressure measuring device 24 is preferably connected to a pressure display and recording device 30, e.g., an instrument sold under the trademark "Datascope 850".

As can be seen from FIG. 1, the distal portion 10 of the catheter, apart from the portion housing the recess 18, is of substantially uniform cross section. As will be explained more fully below, this characteristic facilitates removal of the catheter at the conclusion of monitoring. The ribbon-like shape, e.g., rectangular cross-section, is preferred since it stabilizes the orientation of the catheter, i.e., it minimizes tipping of the distal tip of the catheter such as might disturb the seal formed between sealing portion 19 and the patient's arachnoid membrane 40. In this regard, the width of the back surface 16 at a point behind the recess 18 and of the distal portion 10 should be about 8 millimeters.

The thickness of the distal portion 10 is preferably between about 2 and 4 millimeters. This dimension is important insofar as proper operation of the catheter depends upon sealing contact being effected between sealing surface 19 and the patient's arachnoid membrane, the back of the catheter being supported by the patient's skull 38 through the dura mater 39.

The distal portion should be long enough to be passed through a subcutaneous tunnel of significant length and still have a portion remaining exterior to the skull. Its length should generally be between fifteen and thirty centimeters, preferably between about fifteen and twenty centimeters.

A catheter for pediatric use may be provided by appropriately scaling down the foregoing dimensions. The particular dimensions of such a catheter will depend on the size of the patient for which it is designed. The necessary scaling will be within the skill of those in the art.

To install the catheter, a pair of incisions spaced preferably between about 8 and 12 centimeters apart are made through the patient's scalp 35. A burr hole 32 is drilled through the skull 38 at the site of one of the incisions, and the dura mater 39, but not the arachnoid membrane 40, is penetrated. A subcutaneous tunnel 36 is then formed between the catheter entrance incision 34 and the incision (not shown) adjacent the burr hole 32.

With the stopcock 22 open to the luer hub 27, the catheter is filled with sterilized Ringer's lactated solution containing 100,000 units of bacitracin per liter, and its distal end is introduced into the incision 34 and through the tunnel 36 to the site of the burr hole 32. The catheter lumen 20 is then flushed with more Ringer's solution to clear it and the recess 18 of any substances that may have been introduced while the catheter was being passed through the tunnel 36. The recess should also be visually inspected to make certain that it is clear. The recess 18 is then completely filled with Ringer's lactated solution and the stopcock 22 is closed to prevent fluid leakage from the catheter lumen.

The distal end of the catheter is then inserted through the burr hole 32 and dura mater 39 into the subdural space with the sealing portion 19 in contact with the arachnoid membrane 40. Next, the scalp incision directly above the burr hole 32 is closed, and the catheter is secured to the scalp by sutures. At the same time, a suture can be placed at the incision 34 but left untied for later use after the cup catheter has been withdrawn. An antibiotic ointment with a nonaqueous base is applied liberally at the catheter exit site to prevent infection.

All spaces within the stopcock 22 and within the lines leading to the pressure monitoring device 24 are next completely filled with Ringer's lactated solution, and the 1-3 ml syringe 28 and pressure measuring device 24 are connected. The stopcock is then opened to allow fluid communication between the device 24 and the recess 18.

The pressure measuring device should be positioned at the same height as the patient's cerebral ventricle, and if it becomes necessary for the patient to sit or stand up, either the transducer 24 should be kept level with the patient's cerebral ventricles, or the stopcock should be closed to the syringe to prevent aspiration of fluid into the subdural space. The catheter is now set for monitoring CSF pressure, and any fluctuations will be detected by pressure measuring device 24 and recorded on the pressure recording device 30.

During monitoring, the patient's arachnoid membrane acts as a pressure responsive diaphragm, the steady-state level of the CSF pressure as well as pressure fluctuations affecting the arachnoid membrane being transmitted through the fluid couple to pressure measuring device 24. Pressure waves transmitted through the fluid couple can be caused by normal changes in CSF pressure such as are characteristic of heart beats and respiration, as well as by abnormalities symptomatic of brain damage.

Every two hours, the stopcock 20 should be opened to provide communication between the syringe 28 and the catheter so that, over a period of 5 seconds, a maximum of 0.25 ml of fluid may be injected in the patient's subdural space. During this injection, the seal between the sealing surface 19 and arachnoid membrane 40 is temporarily opened and a small amount of fluid leaks into the subdural space. At the end of the injection and before pressure is released from the syringe, the stopcock should be returned to its original position. This procedure ensures that the recess 18 remains optimally filled with fluid, thereby maintaining the fluid couple from the arachnoid membrane to the pressure measuring device 24.

At the conclusion of monitoring, the retaining sutures connecting the catheter to the scalp are taken out and the catheter is removed by slowly and carefully withdrawing it through the subcutaneous tunnel 36 by pulling on a portion of the catheter external to the scalp. As soon as the catheter is removed, a culture swab should be taken at the cup chamber and at the incision 34. The untied skin sutures at the exit site can now be tied.

In view of the foregoing, it may be seen that several objects of the present invention are achieved and other advantageous results have been attained.

As various changes could be made in the above construction without departing from the scope of the invention, it should be understood that all matter contained in the above description or shown in the accompanying drawings shall be interpreted as illustrative and not in a limiting sense.

What is claimed is:

1. An intracranial pressure monitoring catheter, said catheter having a flexible, ribbon-like distal portion providing flat front and back surfaces, there being a recess in the flat front surface of said portion near the tip thereof and a sealing surface about said recess so that, when the tip of the catheter is inserted through an aperture in a patient's skull and placed between the dura mater and the arachnoid membrane with the back face of the catheter supported by the patient's skull and dura mater, the arachnoid membrane will bridge the recess in the front surface and a seal will be formed between said sealing surface and the arachnoid membrane, said catheter having a longitudinal lumen for providing a fluid couple between said recess and a pressure measuring device, said ribbon-like portion being of essentially constant cross-sectional shape apart from said recess and being of sufficient length to permit the catheter to pass through an incision in the patient's scalp at a point substantially spaced along the skull from said aperture, whereby the catheter may be removed by being drawn longitudinally from the point of exit from the scalp, and spreading of infection from the site of the scalp incision to the skull aperture is inhibited.

2. The catheter as set forth in claim 1 further comprising means for introducing fluid into said lumen.

3. The catheter as set forth in claim 1 wherein said ribbon-like portion is between 2 and 4 millimeters thick and between 15 and 30 centimeters long.

4. An intracranial pressure monitoring catheter comprising:
   a flexible distal portion having flat front and back surfaces;
   a cup-like recess open at said front surface;
   a sealing surface defined by said flat front surface about said recess; and
   a lumen in said distal portion in communication with said recess for providing a fluid couple to a pressure measuring device;
   said catheter being operable to be placed in the patient's subdural space with the patient's dura mater in contact with said back surface and with said sealing surface in contact with the patient's arachnoid membrane, whereby the arachnoid membrane functions as a pressure sensing diaphragm and a fluid couple may be maintained between the patient's arachnoid membrane and a pressure measuring device.

5. The catheter as set forth in claim 4 wherein the thickness of said distal portion is between 2 and 4 millimeters and said back surface has a width of about 8 millimeters.

6. The catheter as set forth in claim 4 wherein said distal portion is elongate and is of essentially uniform cross-sectional shape apart from said recess, whereby the catheter may be installed through a subcutaneous tunnel and may be removed by being drawn longitudinally back through the tunnel.

7. A process for monitoring intracranial pressure in a patient, said process comprising the steps of:
   A. providing apparatus comprising:
      a catheter having a ribbon-like, flexible distal portion having flat front and back surfaces, a cup-like recess open at said front surface adjacent the distal tip of said catheter, a sealing surface defined by said flat front surface about said recess, and a longitudinal lumen in communication with said recess, and
      a pressure measuring device in communication with said recess through said lumen;
   B. inserting the distal portion of said catheter sequentially through a subcutaneous tunnel in the scalp and a hole in the skull of the patient;
   C. positioning the distal tip of said catheter between the dura mater and arachnoid membrane of the patient to contact said sealing portion with the arachnoid membrane so that the arachnoid membrane bridges said recess;
   D. filling said cup-like recess and lumen to provide fluid communication between said recess and said pressure measuring device; and
   E. monitoring the intracranial pressure.

* * * * *